United States Patent [19]

Robson et al.

[11] Patent Number: 5,049,585

[45] Date of Patent: Sep. 17, 1991

[54] CERTAIN 3,3-BIS-(DIFLUORO METHYL)2,2-DIMETHYL-CYCLOPROPANE CARBOXYLATES HAVING INSECTICIDAL ACTIVITY

[75] Inventors: Michael J. Robson, Bracknel; Mark A. Spinney, Wokingham, both of England

[73] Assignee: Imperial Chemical Industries PLC, Millbank, England

[21] Appl. No.: 417,921

[22] Filed: Oct. 6, 1989

[30] Foreign Application Priority Data

Oct. 11, 1988 [GB] United Kingdom ............... 8823764

[51] Int. Cl.$^5$ ................... C07C 69/74; C07C 69/743; A01N 53/00
[52] U.S. Cl. .................................... 514/531; 546/300; 546/302; 548/308; 548/473; 549/453; 560/124
[58] Field of Search ...................... 560/124, 228, 227; 514/461, 531; 549/453

[56] References Cited

U.S. PATENT DOCUMENTS 4,459,305  7/1984  Katsuda ........................... 514/411

FOREIGN PATENT DOCUMENTS 2062620A  5/1981  United Kingdom ............... 514/411

OTHER PUBLICATIONS

Huff et al., *J. C. S. Chem. Comm.*, pp. 742-743 (1980).

*Primary Examiner*—Alan L. Rotman
*Attorney, Agent, or Firm*—Cushman, Darby & Cushman

[57] ABSTRACT

Insecticidal compounds with effective knockdown activity against public health pests and having the general formula:

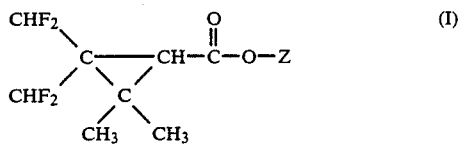

wherein Z is selected from 3-allyl-2-methyl-4-oxocyclopent-2-en-1-yl; 3-propargyl-2-methyl-4-oxocyclopent-2-en-1-yl; 1-ethynyl-2-methylpent-2-en-1-yl; 3,4,5,6-tetrahydrophthalimidomethyl; (6-phenoxypyrid-2-yl)methyl; 1-cyano-1-(6-phenoxypyrid-2-yl)methyl; 1-propargylimidazolin-2,4-dione-3-ylmethyl; 5-benzylfur-3-ylmethyl; and a group of formula:

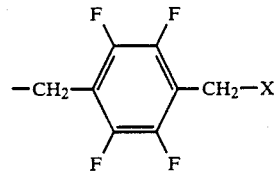

wherein X represents hydrogen, hydroxy, methoxy or ethynyl. The invention also provides processes for the preparation of, and insecticidal compositions comprising, the compounds of formula (I).

7 Claims, No Drawings

CERTAIN 3,3-BIS-(DIFLUORO METHYL)2,2-DIMETHYL-CYCLOPROPANE CARBOXYLATES HAVING INSECTICIDAL ACTIVITY

This invention relates to novel fluorobenzyl esters derived from 3,3-bis-(difluoromethyl)-2,2-dimethylcyclopropanecarboxylic acid, useful in combating insects and similar invertebrate pests, to processes for their preparation, to compositions comprising them and to methods of combating insects and similar invertebrate pests using them.

UK Patent Application No. 2062620 describes certain insecticidal esters derived from 3,3-bis-(difluoromethyl)-2,2-dimethylcyclopropanecarboxylic acid. The compounds of the present invention are novel esters derived from the same carboxylic acid. In addition to their high level of contact, residual and fumigant insecticidal activity, the novel esters show a high level of knockdown activity against a number of public health pests.

In a first aspect, the invention provides compounds having the general formula (I):

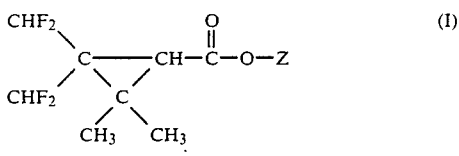

and stereoisomers thereof, wherein Z is selected from
3-allyl-2-methyl-4-oxocyclopent-2-en-1-yl;
3-propargyl-2-methyl-4-oxocyclopent-2-en-1-yl;
1-ethynyl-2-methylpent-2-en-1-yl;
3,4,5,6-tetrahydrophthalimidomethyl;
(6-phenoxypyrid-2-yl)methyl;
1-cyano-1-(6-phenoxypyrid-2-yl)methyl;
1-propargyl-imidazolin-2,4-dione-3-ylmethyl;
5-benzylfur-3-ylmethyl; and a group of formula:

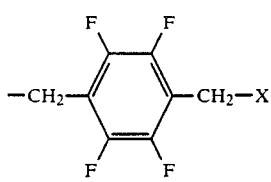

wherein X represents hydrogen, hydroxy, methoxy or ethynyl. Specific compounds according to the invention include those listed below:
3,4,5,6-Tetrahydrophthalimidomethyl 3,3-bis-(difluoromethyl)-2,2-dimethylcyclopropanecarboxylate (hereinafter referred to as Product I);
4-(hydroxymethyl)-2,3,5,6-tetrafluorobenzyl 3,3-bis-(difluoromethyl)-2,2dimethylcyclopropanecarboxylate (hereinafter referred to as Product II);
4-(methoxymethyl)-2,3,5,6-tetrafluorobenzyl 3,3-bis-(difluoromethyl)-2,2dimethylcyclopropanecarboxylate (hereinafter referred to as Product III);
4-(prop-2-yn-1-yl)-2,3,5,6-tetrafluorobenzyl 3,3-bis-(difluoromethyl)-2,2-dimethylcyclopropanecarboxylate (hereinafter referred to as Product IV);
4-methyl-2,3,5,6-tetrafluorobenzyl 3,3-bis-(difluoromethyl)-2,2-dimethylcyclopropanecarboxylate (hereinafter referred to as Product V);
(1RS)-3-allyl-2-methyl-4-oxocyclopent-2-en-1-yl 3,3-bis-(difluoromethyl)-2,2-dimethylcyclopropanecarboxylate (hereinafter referred to as Product VI);
(1RS)-3-propargyl-2-methyl-4-oxocyclopent-2-en-1-yl 3,3-bis-(difluoromethyl)-2,2-dimethylcyclopropanecarboxylate (hereinafter referred to as Product VII);
(1RS)-1-ethenyl-2-methylpent-2-en-1-yl 3,3-bis-(difluoromethyl-2,2-dimethylcyclopropanecarboxylate (hereinafter referred to as Product VIII);
(6-phenoxypyrid-2-yl)methyl 3,3-bis-(difluoromethyl)-2,2-dimethylcyclopropanecarboxylate (hereinafter referred to as Product IX);
1-cyano-1-(6-phenoxypyrid-2-yl)methyl 3,3-bis-(difluoromethyl)-2,2-dimethylcyclopropanecarboxylate (hereinafter referred to as Product X);
1-propargylimidazolin-2,4-dione-3-ylmethyl 3,3-bis-(difluoromethyl)-2,2-dimethylcyclopropanecarboxylate (hereinafter referred to as Product XI);
and 5-benzylfur-3-ylmethyl 3,3-bis-(difluoromethyl-2,2-dimethylcycloprpanecarboxylate (hereinafter refered to as Product XII).

The compounds of the invention are esters and may be prepared by conventional esterification processes, of which the following are examples:

(a) 3,3-bis-(difluoromethyl)-2,2-dimethylcyclpropanecarboxylic acid may be reacted with an alcohol of formula Z0H, where Z has any of the meanings given hereinabove, the reaction preferably taking place in the presence of an acid catalyst, for example dry hydrogen chloride, or a dehydrating agent, for example a carbodiimide such as dicyclohexylcarbodiimide.

(b) A 3,3-bis-(difluoromethyl)-2,2-dimethylcyclopropanecarboxylic acid halide, preferably the acid chloride, may be reacted with an alcohol of formula ZOH, where Z has any of the meanings given hereinabove, the reaction taking place in the presence of a base, for example pyridine, a trialkylamine, an alkali metal hydroxide or carbonate or an alkali metal alkoxide.

(c) 3,3-bis-(difluoromethyl)-2,2-dimethylcyclopropanecarboxylic acid or preferably an alkali metal salt thereof, may be reacted with a halide of formula Z-Hal where Z has any of the meanings given hereinabove and Hal represents a halogen atom, preferably the chlorine or bromine atom, or with the quaternary ammonium salts derived from such halides with tertiary amines, for example pyridine or trialkylamines such as triethylamine.

(d) A lower alkyl ester of 3,3-bis-(difluoromethyl)-2,2-dimethylcyclopropanecarboxylic acid, preferably the methyl or ethyl ester, may be heated with an alcohol of formula ZOH, where Z has any of the meanings given hereinabove, to effect a transesterification reaction. Preferably this process is performed in the presence of a suitable catalyst, for example an alkali metal alkoxide such as sodium methoxide, or an alkylated titanium derivative such as tetramethyl titanante or tetraethyl titanate.

All of these conventional processes for the preparation of esters may be carried out using solvents and diluents for the various reactants where appropriate, and may be accelerated or lead to higher yields of product when performed at elevated temperatures, or in the presence of appropriate catalysts, for example phase transfer catalysts.

The preparation of 3,3-bis-(difluoromethyl)-2,2-dimethylcyclopropanecarboxylic acid and lower alkyl esters thereof by pyrolysis of the pyrazoline obtained by reaction between an alkyl ester of 4,4-difluoro-3-(difluoromethyl)but-2,2-enoic acid and 2-diazopropane has been described by Huff et al in the Journal of the Chemical Society; Chemical Communications, 1980, pp 742–743. This process is summarised in Schemes I and II.

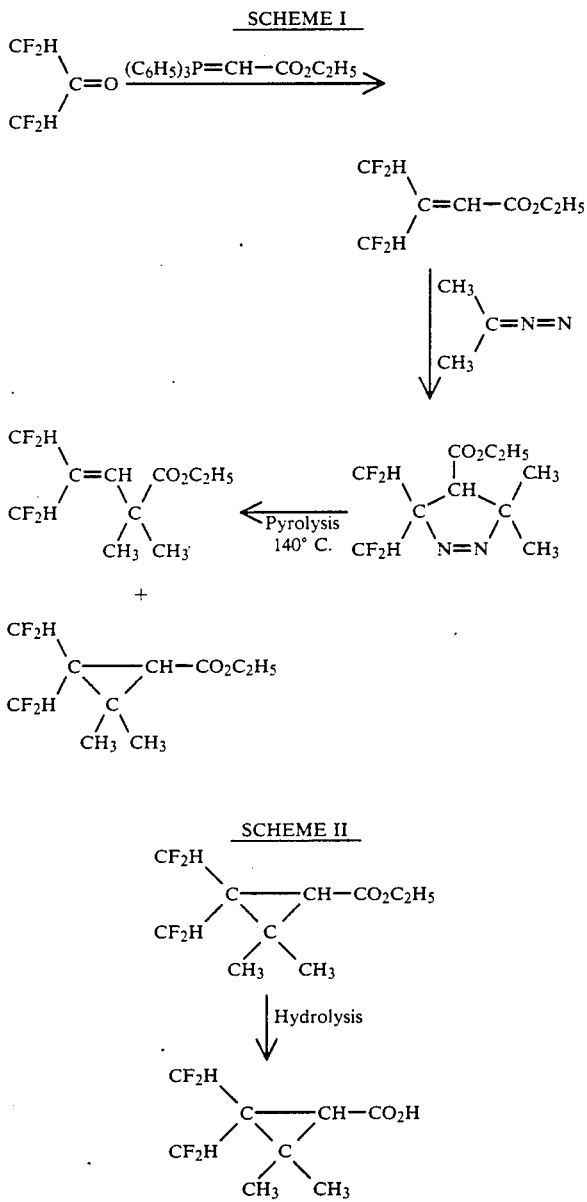

Alcohols of formula ZOH and halides of formula Z-Hal suitable for the preparation of the esters of formula (I) are well known in the art. Thus, for example, the preparation of 4-(prop-2-2,3,5,6-tetrafluorobenzyl alcohol is described in UK Patent Application Number 2171994A, the preparation of 4-(hydroxymethyl)-2,3,5,6-tetrafluorobenzyl bromide is described in UK Patent Application Numoer 2153819A, the preparation of 4-(methoxymethyl)-2,3,4,6tetrafluorobenzyl alcohol is described in European Patent Number 54360, the preparation of 4-methyl-2,3,5,6-tetrafluorobenzyl alcohol is described in European Patent Number 31199, the preparation of N-hydroxymethyl-3,4,5,6-tetrahydrophthalimide is described in Chemical Abstracts, Vol 71 (9), 38400j, the preparation of 1-hydroxy-2-methyl-3-allyl-4-oxocyclopent-2-ene is described by Kawamoto et al in Synthetic Communications, 1975, volume 5, pp 185–191, the preparation of 1-hydroxy-2-methyl-3-propargyl-4-oxocyclopent-2-ene is described by Matsuo et al in Agricultural and Biological Chemistry, 1982, volume 46, pp 1911–1921, the preparation of 1-ethynyl-2-methylpent-2-en-1-ol is described in Japanese patent application No 73/45915, the preparation of (6-phenoxypyrid-2-yl)methanol and of 1-cyano-1-(6-phenoxypyrid-2-yl)methanol are described in UK Patent Application No 1572149 and the preparation of 5-benzyl-3-hydroxymethylfuran is described in French Patent Application No 1503260.

Further details of many of the above processes are given in the Examples hereinafter.

The compounds of formula (I) may be used to combat and control infestations of insect and acarine pests. The insect and acarine pests which may be combated and controlled by the use of rhe invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synegists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repepellency. Additionally multi-component mixtures of this type may help to overcome or prevent the development of resistance to individual components.

The particular insecticide, herbicide or fungicide included in the mixture will depend upon its intended utility and the type of complementary action reguired. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R, 3S)-2,2-dimethyl-3-(2-oxothiolan-3-ylidenemethyl)cyclo-propane carboxylate;

(b) Organophosphates such as profenofos, sulprofos, methyl parathion, azinphos-methyl, demeton-smethyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim, pyrimiphos-methyl, fenitrothion or diazinon;
(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;
(d) Benzoyl ureas such as triflumuron, chlorofluazuron;
(e) Organic tin compounds such as cyhexatin, fenbutatin oxide, azocyclotin;
(f) Macrolides such as avermectins or milbemycins, for example such as abamectin, avermectin, and milbemycin;
(g) Hormones such as juvenile hormone, juvabione, or ecdysones.
(h) Pheromones.
(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentezine, flubenzimine, hexythiazox and tetradifon, motilicides such as dicofol or propargite, acaricides such as bromopropylate, ctlorobenzilate, or insect growth regulators such as hydramethylon, cyromazin, methoprene, chlorofluazuron and diflubenzuron may also be included in the crmpositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect reguired. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liguid preparations to be used as dips, sprays or aerosols. Dips and sprays are generally agueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes.

Wetting agents, dispersing agents and emulsifying agents may be of the cationic, anionic or non-ionic type. Suitable agents of the cationic type include, for example, guaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of agueous dispersions or emulsions are generally supplied in the form of a concentrate containing a high proportion of the active ingredient or ingredients, the said concentrate to be diluted with water before use. These concentrates are often reguired to withstand storage for prolonged periods and after such storage, to be capable of dilution with water to form agueous preparations which remain homogenous for a sufficient time to enable them to be applied by conventional spray equipment. The concentrates may contain 5–95% by weight of the active ingredient or ingredients. When diluted to form agueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of formula (I) and compositions comprising them are very toxic to wide varieties of insect and other invertebrate pests, including, for example, the following:

*Myzus persicae* (aphids)
*Musca domestica* (houseflies)
*Blattella germanica* (cockroaches)
*Periplaneta americana* (cockroaches)
*Blatta orientalis* (cockroaches)

*Spodoptera littoralis* (cotton leaf worm)
*Heliothis virescens* (tobacco budworms)
*Diabrotica spp.* (rootworms)
*Agrotis spp.* (cutworms)
*Nilaparvata lugens* (plant hoppers)
*Nephotettix cincticeps* (plant hoppers)
*Panonvchus ulmi*
*Panonvchus citri*
*Tetranvchus urticae* (red spider mite)
*Tetranychus cinnabarinus* (carmine spider mite)

The compounds according to formula (I) and compositions comprising them have been shown to be particularly useful in controlling lepidopteran pests of cotton, for example Spodoptera spp. and Heliothis spp. They have also been shown to be particularly useful in combating pests which inhabit the soil, for example Diabrotica spp. In addition to their toxic effect, they have also been shown to exhibit high levels of knockdown activity against public health insect pests such as *Musca domestica* (housefly), and *Blattella germanica*. They may also be useful in combating insect and acarine pests which infest domestic animals, such as *Lucilia sericata* and ixodid ticks such as Boophilus spp., Ixodes spp., Amblyomma spp., Rhipicephalus spp., and Dermocentor spp. They are effective in combating both susceptible and resistant strains of these pests in their adult, larval and intermediate stages of growth, and may be applied to the infested host animal by topical, oral or parental administration.

The following Examples illustrate various aspects of this invention. In the preparation Examples the products were usually identified and characterised by means of nuclear magnetic reasonance (NMR) spectroscopy and infra red (IR) spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liguid Chromatography (GLC) retention times were determined on a Hewlett Packard 5890 Gas Chromatograph, using a Chrompak, CPSil 5CB column of 12.5 m length and 0.2 mm internal diameter. Unless otherwise stated, the initial column temperature was 100° C., and a temperature gradient of 15° C./minute employed, up to a maximum temperature of 250° C., maintained for 4 minutes. The carrier gas was helium at a column head pressure maintained at 11 psi. Alternative initial and maximum temperatures are indicated in the Examples where appropriate.

$^1$H Nuclear Magnetic Resonance (NMR) spectrometry was performed at a freguency of 270 MHz on a Jeol FX 270 NMR spectrometer, unless otherwise indicated. 90 MHz, 60 MHz and 400 MHz $^1$H NMR spectrometry as performed using Jeol FX 90Q, Jeol PMX 60SI and Jeol GX400 spectrometers respectively.

$^{19}$F NMR spectrometry was performed on a Jeol FX90Q spectrometer at a freguency of 84.26 MHz. All NMR shift ($\delta$) values are guoted in ppm relative to a standard (TMS or CFCl$_3$).

Molecular Ion (M$^+$) peaks were determined on one of three mass spectrometers : Jeol DX303, Kratos MS80 or Hewlett Packard HP 5992.

EXAMPLE 1

This Example illustrates the preparation of 3,3-bis-(difluoromethyl)-2,2-dimethylcyclopropane carboxylic acid.

A mixture of ethyl 3,3-bis-(difluoromethyl)-2,2-dimethylcyclopropanecarboxylate and ethyl 5,5-difluoro-4-(difluoromethyl)-2,2-dimethylpent-3-enoate (1.85g prepared according to the method of Huff et al, Journal of the Chemical Society, Chemical Communications, 1980, pp 742–743), sodium hydroxide (18 cm3 of a 2 molar agueous solution), and ethanol was stirred vigorously at the ambient temperature (ca 20° C.) for 30 minutes, and then allowed to stand at the ambient temperature for 17 hours.

The mixture was added to water and the aqueous mixture washed with chloroform. The agueous phase was separated and acidified with concentrated agueous hydrochloric acid solution. The resulting emulsion was extracted with chloroform and the organic phase separated, washed with water and dried over anhydrous magnesium sulphate. Evaporation of the solvent under reduced pressure gave a white solid which was recrystallised from chloroform to give the title compound (0.58 g) as colourless crystalline needles. Melting Point: 136°–137° C. $^1$H NMR (CDC13): 6.76, 6.57. 6.37 (1H,t); 6.55, 6.34, 6.14 (1H,t); 2.18 (1H,s); 1.43 (6H,s)

Carbon Analysis: Expected 44.8%.
Found 44.8%.

EXAMPLE 2

The following general method was used to prepare the esters described below from 3,3-bis-(difluoromethyl)-2,2-dimethylcyclopropane carboxylic acid and the appropriate alcohol.

Eguimolar amounts of the acid and the alcohol were mixed in dichloromethane and a catalytic guantity of N,N-dimethylaminopyridine was added to the stirred mixture. An eguimolar amount of dicyclohexylcarbodiimide was added to the stirred mixture at the ambient temperature and progress of the reaction monitored by thin layer chromatography; the reaction was usually complete within 2 hours. On completion of the reaction the solid precipitate was removed by filtration and the filtrate concentrated by evaporation under reduced pressure. The crude reaction product was purified by column chromatography on a silica gel support, eluting with dichloromethane.

The following esters were prepared according to the general method described above.

(i) 4-(methoxymethyl)-2,3,5,6-tetrafluorobenzyl 3,3-bis-(difluoromethyl)-2,2-dimethylcyclopropanecarboxylate (Product III)

90 MHz $^1$H NMR (CDCl$_3$) 7.10, 6.50, 5.90 (1H,3m); 7.00, 6.38, 5.76 (1H,t); 5.25 (2H,s); 4.56 (2H,s); 3.40 (3H,s); 2.22 ($^1$H,s); 1.43 (6H,s).

$^{19}$F MMR (CDCl$_3$): −112 to −122 (4d+s); −143.5 (s).

(ii) 4-(prop-2-yn-1-yl)-2,3,5,6-tetrafluorobenzyl 3, -bis-(difluoromethyl)-2,2-dimethylcyclopropanecarboxylate (Product IV)

MHz $^1$H NMR (CDCl$_3$) 7.07, 6.50, 5.90 (1H,3m); 7.00, 6.36, 5.75 (1H,t); 5.22 (2H,s); 3.63 (2H,d); 2.22 (1H,s); 2.03 (1H,t); 1.43 (6H,s).

$^{19}$F NMR (CDCl$_3$): −113 to 121 (3d+2s); −143.4 (s).

(iii) 3,4,5,6-tetrahydrophthalimidomethyl 3,3-bis-(difluoromethyl)-2,2-dimethylcyclopropanecarboxylate (Product I)

$^1$H NMR (CDCl$_3$): 6.65, 6.45, 6.25 (1H,3d); 6.50, 6.30, 6.10 (1H,t); 5.45 (2H,s); 2.30 (2H,s); 2.10 (1H,s); 1.70 (2H,s); 1.35 (6H,s).

Note: purified by preparative thin layer chromatography on 2 mm silica plates, eluted with dichloromethane.

EXAMPLE 3

This Example illustrates an alternative esterification procedure for the preparation of 2,3,5,6-tetrafluoro-4-(hydroxymethyl)benzyl 3,3-bis-(difluoromethyl)-2,2-dimethylcyclopropane carboxylate (Product II).

A stirred mixture of 3,3-bis-(difluoromethyl)-2,2-dimethylcyclopropanecarboxylate (0.069 g), 2,3,5,6-tetrafluoro-4-(bromomethyl)benzyl alcohol (0.092 g), potassium carbonate (0.056 g) and methyl ethyl ketone (2 cm$^3$) was heated at the reflux temperature for 1.5 hours. Analysis of a withdrawn sample indicated no trace of starting materials after this time. The mixture was cooled, added to water (10 cm$^3$) and the products extracted into ethyl acetate. The organic layer was separated, washed with water, dried over anhydrous magnesium sulphate and the solvent evaporated under reduced pressure to give a colourless oil (0.116 g) which partially crystallised on standing. The crude product was purified by column chromatography to give the title product (0.054 g) as a colourless oil.

GLC Retention Time: 5.47 minutes $^1$H NMR (CDCl$_3$) , 6.72, 6.52, 6.32 (1H,3d); 6.20, 6.40, 6.60 (1H,t); 5.25 (2H,m); 4.87 (2H,d); 2.25 (1H,broad s); 2.05 (1H,t); 1.45 (6H,s). Molecular ion: 406.

EXAMPLE 4

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the tests are given in Table II for each of the Products, at the rate in parts per million given in the second column as a grading of mortality designated as A, B or C wherein A indicates 80–100% mortality, B indicates 50–79% mortality and C indicates less than 50% mortality.

In Table II the pest organism used is designated by a letter code and the pest species, the support medium or food, and the type and duration of test is given in Table I.

TABLE I

| CODE LETTERS (Table IV) | TEST SPECIES | SUPPORT MEDIUM/FOOD | TYPE OF TEST | DURATION (days) |
| --- | --- | --- | --- | --- |
| TUa | *Tetranychus urticae* (spider mites - adult) | French bean leaf | Contact | 3 |
| MP | *Myzus persicae* (aphids) | Chinese Cabbage leaf | Contact | 3 |
| NC | *Nephotettix cincticeps* (green leaf hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| SP | *Spodoptera exigua* (lesser army worm - larvae) | Cotton leaf | Residual | 3 |

"Contact" test indicates that both pests and medium were treated and "residual" indicates that the medium was treated before infestation with the pests.

TABLE II

| PRODUCT | RATE (ppm) | TUa | MP | NC | HV | DB | BG | MD | SP |
| --- | --- | --- | --- | --- | --- | --- | --- | --- | --- |
| I | 100 | — | B* | C* | C | — | C | C** | C |
| II | 100 | — | B* | A* | A+ | — | C | C** | C |
| III | 100 | C | C | A | A | A | A | A | A |
| IV | 100 | C | A | A | A | A | A | A | A |

*Assessed at 2 days after treatment
**Assessed at 3 days after treatment
+Assessed at 5 days after treatment

EXAMPLE 5

This Example illustrates the knockdown activity of the compounds according to the invention.

*Blattella germanica* knockdown test:

The test compound was dissolved in acetone (2 cm$^3$) and the solution diluted to a concentration of 250 ppm with kerosene. 1 cm$^3$ of this preparation was sprayed onto *Blattella cermanica* (adult males) held in a netted plastic pot in a Burkhard Potter Tower. Assessment of knockdown was performed at selected time intervals. On removal from the Burkhard Potter Tower, the insects were held at 25° C. and 65% relative humidity for 48 hours, and an assessment of mortality performed.

Each test was repeated. Results are given in Table IIIA and IIIB.

In Table IIIA, knockdown observations were recorded at intervals of 15 seconds. In Table IIIB, observations were recorded at intervals of 5 minutes.

TABLE IIIA

| TEST COMPOUND | TEST | % KNOCKDOWN OBSERVED AT INTERVALS TIMED IN SECONDS (s) | | | | | | | | | | | % MORTALITY 48 hrs. |
|---|---|---|---|---|---|---|---|---|---|---|---|---|---|
| | | 15 s | 30 s | 45 s | 60 s | 75 s | 90 s | 105 s | 120 s | 135 s | 150 s | 165 s | |
| I | 1 | 10 | 40 | 40 | 60 | 80 | 100 | 100 | 100 | 100 | | | 100 |
| (250 ppm) | 2 | 10 | 30 | 30 | 40 | 60 | 80 | 80 | 100 | 100 | | | 100 |
| | 3 | 0 | 30 | 30 | 40 | 50 | 70 | 70 | 90 | 100 | | | 100 |
| | Mean | 6.7 | 33.3 | 33.3 | 46.7 | 63.3 | 83.3 | 83.3 | 96.7 | 100 | | | 100 |
| II | 1 | 10 | 40 | 60 | 100 | | | | | | | | 100 |
| (250 ppm) | 2 | 10 | 50 | 100 | 100 | | | | | | | | 100 |
| | Mean | 10 | 45 | 80 | 100 | | | | | | | | 100 |

TABLE IIIB

| TEST COMPOUND | TEST | % KNOCKDOWN OBSERVED | | | | % MORTALITY 48 Hours |
|---|---|---|---|---|---|---|
| | | 5 min | 10 min | 15 min | 20 min | |
| Product III | 1 | 100 | | | | 90 |
| (250 ppm) | 2 | 100 | | | | 0 |
| Product IV | 1 | 100 | | | | 100 |
| (250 ppm) | 2 | 100 | | | | 90 |
| Tetramethrin (250 ppm) | * | 80 | 100 | | | 50 |

*Meaned values from 24 observations

*Musca domestica* knockdown test (method 1)

The test compound was dissolved in acetone and the solution diluted with kerosene to give a concentration of 250 ppm. 1 cm³ of this preparation was sprayed on to *Musca domestica* (adult females) held in a netted plastic pot in a Burkhard Potter Tower. Assessment of knockdown was performed at 15 second intervals. On removal from the Burkhard Potter Tower, the insects were held at 25° C. and 65% relative humidity for 48 hours, and an assessment of mortality was performed. Each test was repeated. Results are given in Table IVA.

(method 2)

1 cm³ of a 30 ppm solution of the test chemical in acetone was sprayed into a Kearns and March chamber containing 20 *Musca domestica* (adult females). Knockdown was observed over a period of 10 minutes and $KT_{50}$ and $KT_{90}$ values (the time taken for 50% and 90% of the insects to be knocked down) were calculated from the observations. The results given in Table IVB represent average KT values of 3 replicates except where otherwise stated.

TABLE IVB

| TEST COMPOUND | KT50 (Mins) | KT90 (Mins) |
|---|---|---|
| Product III (30 ppm) | 2.04 | 4.06 |
| Product IV (30 ppm) | 2.53 | 4.22 |
| Tetramethrin (30 ppm) | 3.94* | 8.78* |

*Indicates average of results of 6 replicates

We claim:

1. A compound of formula:

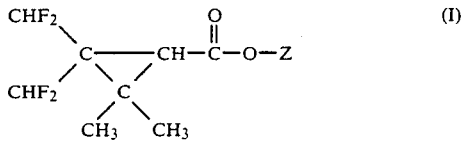

(I)

and stereoisomers thereof, wherein Z is selected from:

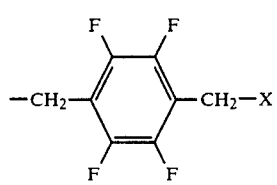

wherein X represents hydrogen, hydroxy, methoxy or ethynyl.

TABLE IVA

| TEST COMPOUND | TEST | % KNOCKDOWN OBSERVED AT INTERVALS TIME IN SECONDS (s) | | | | | | | | | | | % MORTALITY 48 hrs. |
|---|---|---|---|---|---|---|---|---|---|---|---|---|---|
| | | 15 s | 30 s | 45 s | 60 s | 75 s | 90 s | 105 s | 120 s | 135 s | 150 s | 165 s | |
| I | 1 | 20 | 40 | 40 | 80 | 100 | | | | | | | 100 |
| (250 ppm) | 2 | 0 | 40 | 60 | 100 | 100 | | | | | | | 100 |
| | 3 | 20 | 50 | 90 | 100 | 100 | | | | | | | 100 |
| | Mean | 13.3 | 43.3 | 63.3 | 93.3 | 100 | | | | | | | 100 |
| II | 1 | 10 | 10 | 10 | 30 | 40 | 50 | 60 | 90 | 90 | 90 | 100 | 100 |
| (250 ppm) | 2 | 0 | 10 | 30 | 30 | 40 | 40 | 60 | 90 | 100 | 100 | 100 | 100 |
| | 3 | 0 | 0 | 20 | 40 | 60 | 70 | 80 | 90 | 100 | 100 | 100 | 100 |
| | Mean | 3.3 | 6.7 | 20 | 33.3 | 46.7 | 53.3 | 66.7 | 90 | 96.7 | 96.7 | 100 | 100 |

2. 3,4-(Hydroxymethyl)-2,3,5,6-tetrafluorobenzyl 3,3-bis-(difluoromethyl)-2,2-dimethylcyclopropanecarboxylate.

3. 4-(Methoxymethyl)-2,3,5,6-tetrafluorobenzyl 3,3-bis-(difluoromethyl)-2,2-dimethylcyclopropanecarboxylate.

4. 4-(Prop-2-yn-1-yl)-2,3,5,6-tetrafluorobenzyl 3,3-bis-(difluoromethyl)-2,2-dimethylcyclopropanecarboxylate.

5. 4-Methyl-2,3,5,6-tetrafluorobenzyl 3,3-bis-(difluoromethyl)-2,2-dimethylcyclopropanecarboxylate.

6. An insecticidal composition comprising an insecticidally effective amount of a compound according to claim 1 in association with an insecticidally inert diluent or carrier.

7. A method of combating insect pests at a locus which comprises treating the locus with an insecticidally effective amount of the composition of claim 6.

* * * * *